US010617832B2

(12) United States Patent
Mangold et al.

(10) Patent No.: US 10,617,832 B2
(45) Date of Patent: Apr. 14, 2020

(54) HIGH PRECISION, LOW DOSE ATOMIZER

(71) Applicant: Southwest Research Institute, San Antonio, TX (US)

(72) Inventors: Barrett Wade Mangold, Hondo, TX (US); Terrence Francis Alger, II, San Antonio, TX (US); Albert M. Zwiener, Helotes, TX (US)

(73) Assignee: Southwest Research Institute, San Antonio, TX (US)

( * ) Notice: Subject to any disclaimer, the term of this patent is extended or adjusted under 35 U.S.C. 154(b) by 329 days.

(21) Appl. No.: 15/821,072

(22) Filed: Nov. 22, 2017

(65) Prior Publication Data

US 2019/0151574 A1 May 23, 2019

(51) Int. Cl.
*A61M 11/06* (2006.01)
*A61M 15/00* (2006.01)
(Continued)

(52) U.S. Cl.
CPC ........ *A61M 11/06* (2013.01); *A61M 15/0001* (2014.02); *A61M 31/00* (2013.01);
(Continued)

(58) Field of Classification Search
CPC ...... A61M 11/06; A61M 35/00; A61M 31/00; A61M 15/0001; A61M 2210/0612; A61M 11/007; A61M 2210/065; A61M 2210/0662; A61M 2210/0618; A61M 15/08; B05B 11/0064; B05B 11/02;
(Continued)

(56) References Cited

U.S. PATENT DOCUMENTS 2,564,400 A 8/1951 Hall
3,517,525 A * 6/1970 Campbell .............. F25J 1/0276 62/222

(Continued)

FOREIGN PATENT DOCUMENTS

EP 1427538 B1 7/2008

OTHER PUBLICATIONS

Aptar pharma UDS/BDS (4 pgs) <<https://pharma.aptar.com/sites/default/files/products/marketing_sheet/files/pds_udsandbds.pdf>> (accessed Nov. 21, 2017).

(Continued)

*Primary Examiner* — Michael J Tsai
*Assistant Examiner* — Rachel H. Moon
(74) *Attorney, Agent, or Firm* — Grossman, Tucker, Perreault & Pfleger, PLLC

(57) ABSTRACT

An adapter for delivering an atomized spray from a syringe. The adapter includes an adapter guide including a side wall, an interior surface of the side wall defining a through-bore and a shoulder in the through-bore. A pin guide is located in the through-bore. The pin guide includes a seat and a sleeve extending from the seat. A spring positioned around the pin guide sleeve and between the pin guide seat and the shoulder, wherein the spring and the sleeve provide a passageway there between. A pin extends from the pin guide seat and through the passageway. Affixing the adapter onto a syringe provides an atomizing delivery device. A method of dispensing an atomized spray from a syringe is provided by affixing the adapter to the syringe.

19 Claims, 6 Drawing Sheets

(51) Int. Cl.

| | |
|---|---|
| ***A61M 31/00*** | (2006.01) |
| ***B05B 11/02*** | (2006.01) |
| ***B05B 11/00*** | (2006.01) |
| ***A61M 35/00*** | (2006.01) |
| *A61M 15/08* | (2006.01) |
| *A61M 11/00* | (2006.01) |

(52) U.S. Cl.

CPC ......... *A61M 35/00* (2013.01); *B05B 11/0064* (2013.01); *B05B 11/02* (2013.01); *A61M 11/007* (2014.02); *A61M 15/08* (2013.01); *A61M 2210/065* (2013.01); *A61M 2210/0612* (2013.01); *A61M 2210/0618* (2013.01); *A61M 2210/0662* (2013.01); *B05B 11/0008* (2013.01)

(58) Field of Classification Search

CPC ....... B05B 11/0008; B05B 1/12; B05B 1/262; B05B 1/265; B05B 1/267; B05B 1/3006; B05B 1/3073; B05B 1/323; B05B 3/0486; B05B 7/1254; A62C 31/02; Y10S 239/01; Y10T 137/7722; Y10T 137/7837

USPC ....... 239/570, 505, 506, 507, 512, 513, 514, 239/515, 518

See application file for complete search history.

(56) References Cited

U.S. PATENT DOCUMENTS

| | | | | |
|---|---|---|---|---|
| 3,894,691 | A * | 7/1975 | Mee | A01G 13/065 239/524 |
| 4,923,448 | A | 5/1990 | Ennis, III | |
| 5,289,818 | A | 3/1994 | Citterio et al. | |
| 5,328,099 | A | 7/1994 | Petit et al. | |
| 5,370,317 | A | 12/1994 | Weston | |
| 5,662,271 | A | 9/1997 | Weston et al. | |
| 5,722,953 | A | 3/1998 | Schiff et al. | |
| 6,053,894 | A | 4/2000 | Shadd, Jr. | |
| 6,112,743 | A | 9/2000 | Denton | |
| 6,182,904 | B1 | 2/2001 | Elcyznski et al. | |
| 6,250,509 | B1 * | 6/2001 | Fuchs | B05B 11/0059 222/321.6 |
| 6,402,055 | B1 | 6/2002 | Jaeger et al. | |
| 6,425,499 | B1 | 7/2002 | Guiffray | |
| 6,626,379 | B1 * | 9/2003 | Ritsche | B05B 11/0078 239/303 |
| 6,698,429 | B2 | 3/2004 | Croll et al. | |
| 6,708,846 | B1 | 3/2004 | Fuchs et al. | |
| 6,866,039 | B1 | 3/2005 | Wright et al. | |
| 7,389,947 | B2 | 6/2008 | Denton | |
| 8,210,166 | B2 | 7/2012 | Denton et al. | |
| 8,419,706 | B2 | 4/2013 | Heldt et al. | |
| 8,987,496 | B1 | 3/2015 | McDonough et al. | |
| 9,151,281 | B2 * | 10/2015 | Donnette | F04B 9/08 |
| 9,216,222 | B2 | 12/2015 | Zwiener et al. | |
| 9,265,898 | B2 | 2/2016 | Rajan et al. | |
| 2002/0174865 | A1 | 11/2002 | Gatton, Jr. et al. | |
| 2007/0113841 | A1 * | 5/2007 | Fuchs | A61F 9/0008 128/200.14 |
| 2010/0022965 | A1 * | 1/2010 | Salzman | A61M 5/3129 604/207 |
| 2010/0179511 | A1 | 7/2010 | Rajan et al. | |
| 2012/0199119 | A1 | 8/2012 | Pardonge | |
| 2013/0096493 | A1 * | 4/2013 | Kubo | A61M 3/0262 604/58 |
| 2013/0175303 | A1 * | 7/2013 | Donnette | B05B 11/3004 222/321.6 |
| 2013/0277443 | A1 | 10/2013 | Croll et al. | |
| 2013/0298902 | A1 | 11/2013 | Denton et al. | |
| 2015/0274386 | A1 * | 10/2015 | Ritsche | B05B 11/047 222/335 |
| 2015/0352301 | A1 * | 12/2015 | Stedman | A61M 11/007 128/200.16 |
| 2016/0318051 | A1 | 11/2016 | Petit et al. | |
| 2017/0072147 | A1 * | 3/2017 | Eicher | A61M 15/0081 |

OTHER PUBLICATIONS

Teleflex: LMA +EMS, LMA MAD Nasal; Intranasal Mucosal Atomization Device (2 pgs) <<https://www.teleflex.com/en/usa/productAreas/ems/documents/EMS_LMA_MADNasal_DS_2013-2162.pdf>> (accessed Nov. 21, 2017).

* cited by examiner

HIGH PRECISION, LOW DOSE ATOMIZER

GOVERNMENT SUPPORT CLAUSE

This invention was made with United States Government support under Contract No. HHSO100201100038C awarded by the Department of Health and Human Services, Assistant Secretary for Preparedness and Readiness, Office of Acquisitions Management, Contracts and Grants. The Government has certain rights in this invention.

FIELD

The present disclosure is directed to an adapter to retrofit a syringe to deliver an atomized spray, an atomizing delivery device including the adapter and a syringe, and a method of dispensing a liquid formulation from the atomizing delivery device.

BACKGROUND

Atomizers are useful for the delivery of pharmaceutical compositions to the nose, eye, ear, throat or other body parts. Hypodermic syringes may be capable of administering relatively repeatable and accurate dosages of pharmaceutical compositions, but without modification may deliver such compositions in the form of a stream, with or without a needle present. Nozzle tips have been provided for the adaptation of a syringe, which provide an atomized spray upon advancement of the syringe plunger. In some cases, atomization is provided through the provision of a plurality of narrow passages in the nozzle tip that imparts turbulence to the flow of the pharmaceutical composition, breaking up the stream of liquid that exits the syringe into particles. In some cases, the adapter is configured to impart a rotational component of velocity in the discharging liquid. However, further improvement in dosing repeatability and accuracy remains desirable.

SUMMARY

An aspect of the present disclosure relates to an atomizing delivery device. The device includes an adapter and a syringe. The syringe includes a barrel and a cannula extending from the barrel. The cannula includes a terminal opening which is in fluid communication with the barrel. The adapter includes an adapter guide including a side wall, an interior surface of the side wall defining a through-bore and a shoulder in the through-bore, wherein the cannula is received in the through-bore. The adapter also includes a pin guide, which includes a seat and a sleeve extending from the seat. The pin guide is located in the through-bore and surrounds a portion of the cannula. The adapter further includes a spring located around the pin guide sleeve and between the pin guide seat and the shoulder, wherein the spring and the sleeve provide a passageway there between. The adapter further includes a pin, which extends through the passageway from the pin guide and the pin is seated on the cannula terminal opening.

Another aspect of the present disclosure relates to an adapter for delivering an atomized spray from a syringe. The adapter includes an adapter guide including a side wall, an interior surface of the side wall defining a through-bore and a shoulder in the through-bore. A pin guide is located in the through-bore. The pin guide includes a seat and a sleeve extending from the seat. A spring positioned around the pin guide sleeve and between the pin guide seat and the shoulder, wherein the spring and the sleeve provide a passageway there between. A pin extends from the pin guide seat and through the passageway.

A further aspect of the present disclosure relates to a method of dispensing an atomized spray from a syringe. The method includes affixing the above described adapter to a syringe, which includes a barrel, including a liquid formulation, and a cannula, which includes a terminal opening in fluid communication with the barrel, extending from the barrel. The adapter includes an adapter guide including a side wall, an interior surface of the side wall defining a through-bore and a shoulder in the through-bore, wherein the cannula is inserted into the through-bore. The adapter further includes a pin guide including a seat and a sleeve extending from the seat located in the through-bore, wherein a portion of the cannula is passed through the pin guide. The adapter further includes a spring positioned around the pin guide sleeve and between the pin guide seat and the shoulder, wherein the spring and the sleeve provide a passageway there between. The adapter also includes a pin extending through the passageway from the pin guide and the pin is seated on the terminal opening. The method further includes dispensing the liquid formulation from the syringe.

BRIEF DESCRIPTION OF THE DRAWINGS

The above-mentioned and other features and advantages of the present disclosure, and the manner of attaining them, will become appreciated and be more readily understood by reference to the following detailed description in conjunction with the accompanying drawings, wherein.

DETAILED DESCRIPTION

The present disclosure is directed to an adapter to retrofit a syringe to deliver an atomized spray, an atomizing delivery device including the adapter and a syringe, and a method of dispensing a liquid formulation from the atomizing delivery device. Preferably, the device delivers a dose of a liquid formulation in the range of 5 to 100 μL+/−10% of the dose (relative standard deviation). Adapter geometry may be configured to retrofit commercially available syringes. Generally, the adapter includes a pin that is held against the opening of a cannula extending from a syringe under the force of a spring. Upon dispensing a liquid formulation from the syringe, the spring maintains the pin on the cannula opening until the spring force is overcome by the force on the liquid formulation. The force on the liquid formulation pushes the pin back from the cannula and the liquid formulation is atomized upon exiting the cannula.

Figure 1:
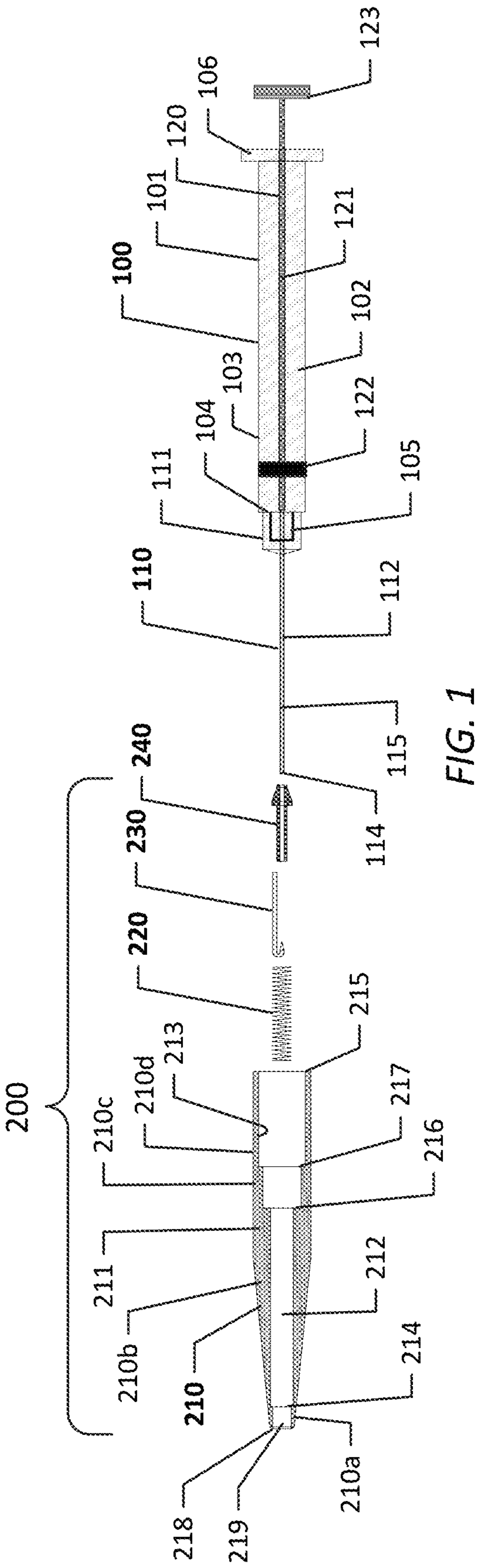
FIG. 1 is an exploded view of a cross-section schematic of an embodiment of an adapter and a syringe.
Figure 2:
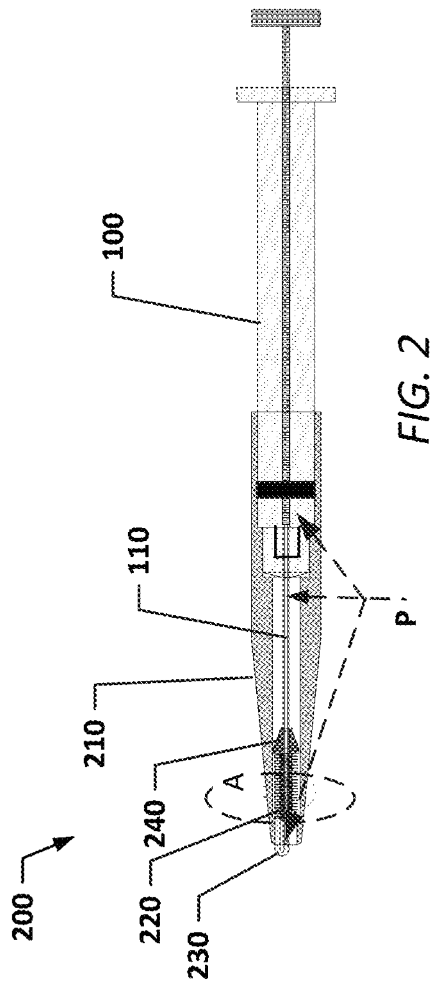
FIG. 2 is a cross-section schematic view of an embodiment of an atomizing delivery device including the adapter affixed to the syringe.

FIG. 1 illustrates an exploded view of an embodiment of the adapter and a syringe and FIG. 2 illustrates an assembled embodiment of the adapter mounted on the syringe. The syringe 100 generally includes a barrel 101 including a bore 102 defined therein by the barrel side wall 103 and at least one end wall 104. A syringe tip 105 extends from the barrel end wall 104. While not illustrated, a second end wall opposing the first end wall 104 and syringe tip 105 may be present to seal the end of the syringe around the plunger 120. The barrel may optionally include a flange 106, which is preferably located at the distal end of the barrel opposing the syringe tip 105. The syringe may be formed from a polymer material, such as polypropylene, polypropylene co-polymers, cyclo-olefin polymers, or cyclo-olefin copolymers, or from glass.

As illustrated, the plunger 120 includes a plunger stem 121 that extends into the syringe bore 102, a plunger tip 122 that forms an interference fit, i.e., a friction or press fit, with the interior of the barrel wall 103, and a plunger actuator 123. In preferred embodiments, the syringe holds a liquid volume of 100 μL or less, such as in the range of 5 μL to 100 μL. However, syringes up to 1,000 μL may be employed, including all values and increments therein and particularly from 5 μL to 100 μL, 100 μL to 1,000 μL, etc. The plunger may be formed from a polymer material, such as polypropylene, polypropylene co-polymers, cyclo-olefin polymers, or cyclo-olefin copolymers. The plunger may be manually operated or automated.

Further, the syringe may include a number of tip styles 105 that, in embodiments, connect to the needle 110, as illustrated. The needle, e.g., includes a hub 111 and the cannula 112, which may be understood as an elongate tube including a passage 115 there through. The cannula 112 gauge may be, for example, in the range of 30 to 16, including all values therein. The needle hub 111 and syringe tip 105 are fastened together using a friction fit, wherein the syringe tip may include a luer tip, which is received within the needle hub 111. Alternatively, the needle may be affixed to the syringe by mating mechanical fasteners, such as by threads or undercuts; by an adhesive; by welding; or through a combination of the above. Further, the needle may be affixed to the syringe without the presence of a needle hub. It may also be appreciated that while needle cannulas are often formed from metallic materials, the cannula may be formed from other materials such as a ceramic or a thermoplastic material. In other, alternative embodiments, the cannula is formed from the syringe tip, wherein the tip may be a catheter style tip, and the hub may, again, be omitted. Such cannulas may exhibit the same gage as those described above. The terminal opening 114 of cannula 112 may be blunt or beveled. It may be appreciated that the configuration of the terminal opening of the needle cannula may affect the spray pattern of the adapter. Fluid communication through a flow path P (illustrated in FIG. 2) is provided from the barrel, through the cannula and through the terminal opening of the cannula.

The adapter 200 may generally include an adapter guide 210, a spring 220, a pin 230, and a pin guide 240. In the illustrated embodiment, the cannula 112 of the needle 110, the needle hub 111, the syringe tip 105, and at least a portion of the barrel 101 are received in the adapter, wherein the adapter guide 210 and syringe 100 are mechanically affixed together via a friction fit. However, the adapter guide 210 may also, or alternatively, be mechanically affixed to the syringe via mating features provided on the adapter and syringe to mechanically fasten the adapter to the syringe. For example, threads may be provided on the interior of the adapter guide side wall 211 that mate with threads provided on the exterior of the needle hub 111 or syringe tip 105. Accordingly, one may appreciate that the adapter guide 210 is a structural component that serves to locate the spring, pin and pin guide relative to the cannula of the syringe. The pin guide 240 may be understood as a structural component to receive the cannula and which engages with the spring and pin. As illustrated in FIG. 1, the adapter guide 210 generally includes four portions 210*a*, 210*b*, 210*c*, and 210*d* defined by a side wall 211 defining a through-bore 212 therein. The interior surface of the side wall 213 defines a number of steps or shoulders 214, 216, 217, where the diameter of the bore 212 is reduced from the proximal end of the adapter guide 215 (proximal to the syringe) to the distal end of the adapter guide 218 (distal from the syringe). These transitions define the four portions of the adapter guide 210. It may be appreciated that fewer or greater than four portions of the adapter guide may be present, depending on the configuration of the adapter guide and configuration of the syringe receiving the adapter guide.

The first portion 210*a* of the adapter guide is provided between the first shoulder 214 and the distal end 218 of the adapter guide 210. The through-bore 212 in this portion of the adapter guide 210 exhibits the smallest diameter. In preferred embodiments, the diameter of this portion of the adapter guide may be the same as the inner diameter of the spring 220. An opening 219 is present at the distal end 218 of the adapter guide 210.

A second portion 210*b* of the adapter guide 210 is defined between the first shoulder 214 and second shoulder 216. In addition, the through-bore 212 in this portion of the adapter guide 210 exhibits a second diameter that is larger than the first diameter and larger than the diameter of the pin guide 240. The first shoulder 214 provides an abutment for a first end of the spring 220. In optional embodiments, the spring 220 is affixed to the first shoulder 214 to prevent the spring, pin and pin guide from falling out of the adapter 200.

The second shoulder 216 provides a stop for the needle hub 111, wherein the needle hub 111 abuts the second shoulder 216. The region between the second shoulder 216 and a third shoulder 217 defines the third portion 210*c* of the adapter guide. The through-bore 212 in this portion of the adapter guide exhibits a third diameter that is larger than that of the first and second diameters and, in preferred embodiments, slightly larger than the outer diameter of the needle hub 111 or syringe tip 105, such as in the range of 0.1% to 5.0% greater than the diameter of needle hub 111 or syringe tip 105.

The third shoulder 217 is illustrated as creating a stop for receiving the end wall 104 of the syringe, wherein the syringe end wall 104 abuts the third shoulder 217 when the adapter is positioned over the syringe. A fourth portion 210*d* of the adapter guide 210 is provided between the proximal end 215 of the adapter guide and the third shoulder 217. In this portion 210*d*, the adapter guide 210 exhibits a fourth diameter, which in preferred embodiments is slightly larger in diameter than the outer diameter of the syringe, such as in the range of 0.1% to 5% greater than the diameter of the syringe. In embodiments, the fourth portion 210*d* of the adapter guide (between the third shoulder 217 and the proximal end 215 of the adapter guide) may be omitted, such as when the adapter is mechanically affixed to the needle hub 111 or the syringe tip 105. If the fourth portion 210*d* of the adapter guide is omitted, the proximal end of the adapter is located where the third shoulder 217 is illustrated.

Figure 3:
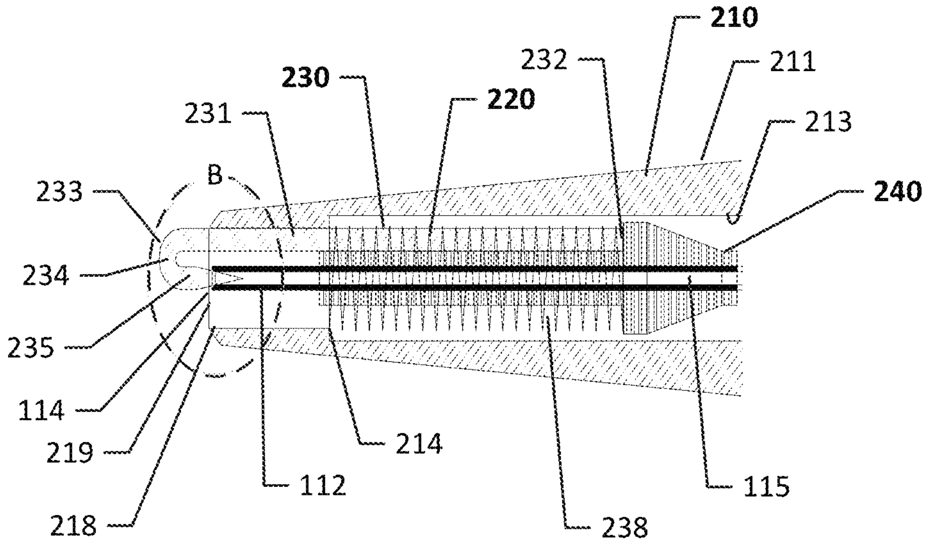
FIG. 3 is a close up view of detail A of FIG. 2.

With reference to FIG. 3, the spring 220 is preferably a compression spring, which is understood to be naturally at rest in an extended state. The spring retains the pin relative to the cannula to seal the terminal opening of the cannula wherein, the spring may or may not be initially loaded against the cannula under compression. The spring may be selected such that a sufficient force may be exerted on the liquid formulation as the liquid formulation is dispensed from the syringe to cause atomization of the liquid formulation when the liquid formulation unseats the pin 230 and is released from the cannula 112 needle. Unseating of the pin 230 from the cannula terminal opening further compresses the spring 220 as the pin guide 240 moves toward the first shoulder 214 with the pin 230 and compresses the spring 220. The spring 220 may be formed from any number of materials, including metal, a metal alloy, or a polymer material such as rubber including natural rubber, silicon rubber, or a thermoplastic elastomer. While a coil spring is illustrated, the spring may alternatively exhibit other configurations, such as a wave spring or if the spring is formed from rubber, the spring may be in the form of a cylinder. In addition to holding the pin 230 relative to the cannula 112, the spring serves to define a passage 238 for the pin 230 between the spring 220 and the pin guide sleeve 242.

Figure 4:
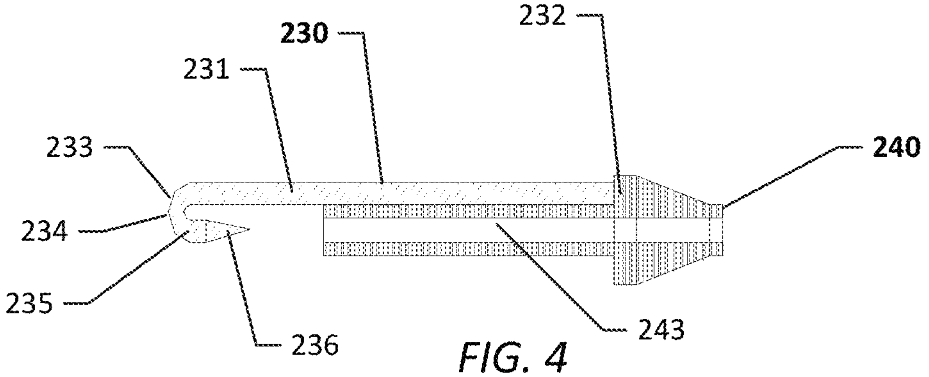
FIG. 4 is cross-sectional view of an embodiment of a pin and a pin guide.

As illustrated in FIGS. 3 and 4, the pin 230 preferably exhibits a "hook" or "J" shape and sits on the end of the terminal opening of the needle 110 and, in preferred embodiments, is received, at least partially within the terminal opening of the needle 110. As noted above, the pin 230 is held onto the terminal opening of the cannula 112 by the spring 220 and pin guide 240. The pin 230 includes a stem 231. The proximal end 232 of the stem (relative to the syringe) is mounted in the pin guide 240. The stem 231 is preferably mechanically affixed to the pin guide, such as via a friction fit wherein a retention hole is provided in the pin guide, or the pin is adhered to or welded into the pin guide. In preferred embodiments, the distal end of the stem 233 includes a bend 234 that forms an arm 235 extending from the stem 233. The arm is substantially parallel to the stem 233.

Figure 5:
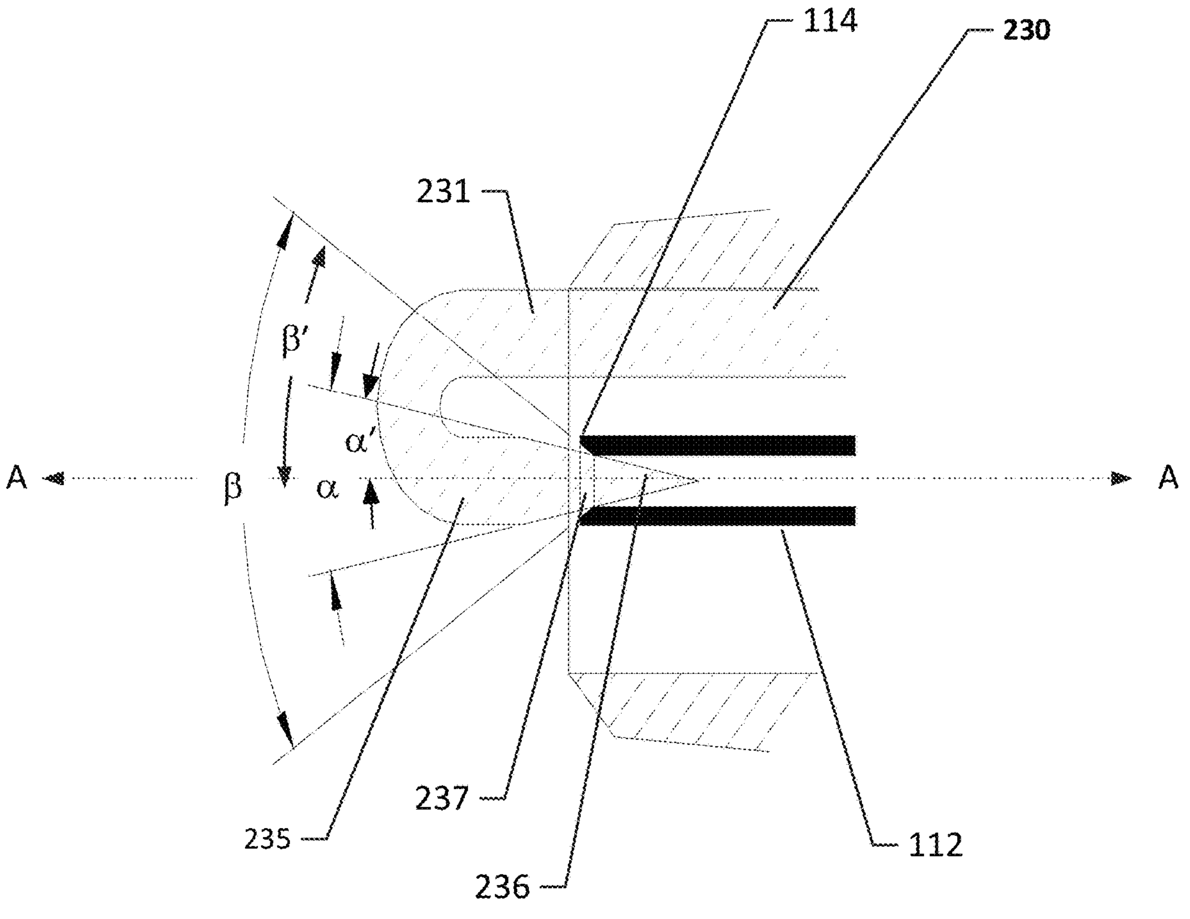
FIG. 5 is a close up view of detail B of FIG. 3.

The end of the arm 235 preferably includes a conical tip 236 as illustrated in FIG. 5. The conical tip may exhibit an angle α of 5 to 30 degrees including all values and ranges therein, or an angle α' of 2.5 to 15 degrees as measured from axis A-A which extends through the longitudinally, through the center of the arm 235. Between the conical tip 236 and the arm 235 is preferably a truncated cone. The truncated cone 237 exhibits an angle β that is greater than the angle of the conical tip 236, which may be in the range of 30 degrees to 120 degrees from the tip formed by the conical tip 236, or an angle β' of 15 to 60 degrees from axis A-A, including all values and ranges therein.

The pin may exhibit any number of cross-sectional geometries and individual portions of the pin, i.e., the stem and arm, may exhibit different cross-sectional geometries. For example, the stem and arm may be flat yet terminate in the conical tip, or the stem may be flat and the arm may be circular terminating in the conical tip. In alternative embodiments, rather than a cone tip, other geometries may be provided for the arm terminus. For example, the conical tip may be replaced with a hemispherical geometry or the end of the arm may be flat. Further, fluting, i.e., channels, may be formed in the pin arm 235 surface to assist in atomizing the liquid formulation. The pin may be formed from a number of materials such as a metal, metal alloy, or polymer material such as polycarbonate, acrylic, polyethylene or polypropylene.

Figure 6:
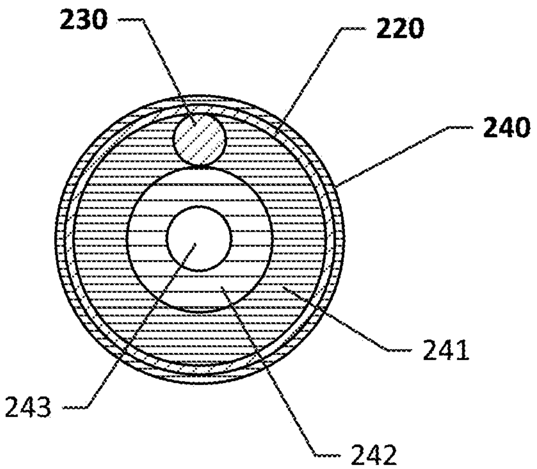
FIG. 6 is a top view of an embodiment of a pin seat.
Figure 7:
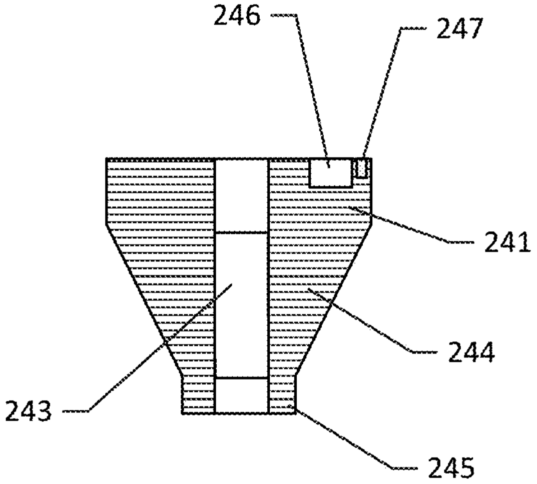
FIG. 7 is a side, cross-section of an embodiment of the pin seat of FIG. 6.

Turning to FIGS. 4, 6 and 7 the pin guide 240 includes a through-bore 243 so that the pin guide may slide over the cannula 112. As alluded to above, the pin guide 240 provides a seat 241 for the spring 220 and the pin 230. Extending from the seat 241 is a sleeve 242, which extends longitudinally and generally parallel to the cannula. The external diameter of the sleeve 242 is relatively smaller than the internal diameter of the spring 220, so as to provide a passage 238 for the pin between the spring 220 and the sleeve 242 (see FIG. 3). As illustrated in FIG. 7, the pin guide 240 includes four sections, the seat 241 that is cylindrical, the sleeve 242 that extends from the seat 241, a truncated cone 244 opposing the sleeve relative to the seat, and a second cylindrical portion 245 opposing the first cylindrical portion relative to the truncated cone. The second cylindrical portion has a reduced diameter from the first cylindrical portion; however, in alternative embodiments the diameter of the first and second cylindrical portions maybe the same. However, the pin guides may assume other geometries.

The stem 231 of the pin is affixed to the pin guide 240. In preferred embodiments, the pin guide 240 includes a channel 246 defined in the pin seat for receiving an end of the spring therein and a bore 247 for receiving the stem of the pin. In optional embodiments, the spring is affixed to the pin guide 240. The geometry of the pin, spring and pin guide may be selected and adjusted for a particular cannula and cannula opening.

When assembled the pin guide and spring sit in the second portion of the through-bore of the adapter guide, surrounding the cannula. The pin is located in the first and second portions of the adapter guide and preferably extends out of the first portion of the adapter guide and through the hole at the end of the adapter guide. The needle may also extend to the end of the adapter guide or may be recessed within the adapter guide. Again, interaction of the spring between the first shoulder and the pin guide hold the pin against the terminal opening of the cannula under the compressive spring force.

Figure 8:
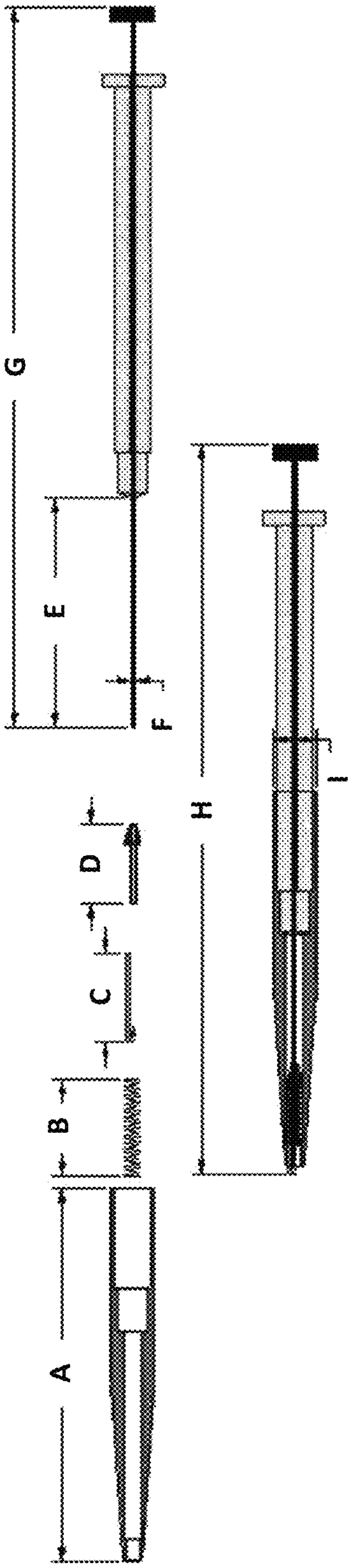
FIG. 8 is an embodiment of the dimensions of an adapter and syringe employed in the Example testing.

A particular embodiment of the adapter and a syringe is illustrated in FIG. 8 and Table 1 wherein, with reference to FIGS. 1 and 2, A is the length of the adapter 210, B is the length of the spring 220, C is the length of the pin 230, D is the length of the pin guide 240, E is the length of the needle 110, F is the diameter of the needle 110 (measured at the exterior surface), G is the length of the syringe 100, H is the length of the assembled needle and adapter, and I is the diameter of the syringe barrel 101 (measured at the exterior surface).

TABLE 1

| Syringe Dimensions (in inches) | | | | | | | | |
|---|---|---|---|---|---|---|---|---|
| A | B | C | D | E | F | G | H | I |
| 3.250 | 0.850 | 0.772 | 0.695 | 1.994 | 0.028 | 6.265 | 6.353 | 0.375 |

Note that the dimensions provided in this particular embodiment are non-limiting. Each dimension may be independently adjusted based on the size of the syringe and needle.

In an embodiment of using the adapter, the syringe may be loaded with the desired amount of a liquid formulation. Preferably, the formulation may include a pharmaceutical composition of one or more pharmaceutical agents, i.e., a compound used for medicinal purposes, including those for treating or preventing diseases or other conditions. Such pharmaceutical agents may include, but are not limited to compositions for treating viral, bacterial, allergic, wounds, ulcers, lesions, inflammation, abnormal growths, build-up of secretions, etc. The pharmaceutical composition may be liquid or solid particles. The pharmaceutical compositions may also be provided in a liquid carrier, such as an aqueous carrier or an oil based carrier. Further, the pharmaceutical composition may include additives such as solvents, dispersants, stabilizing agents, preservatives, colorants, odorants, or flavorants.

The adapter is slipped over the needle and secured to the syringe. The liquid formulation is then dispensed from the syringe. A force is applied to the liquid formulation, such as when the syringe plunger is pressed towards the syringe tip. Under sufficient pressure the liquid formulation unseats the pin from the terminal opening of the cannula and the liquid formulation flows around the tip of the pin creating an atomized spray. An atomized spray may be understood as the result of breaking up a liquid into droplets that then can be moved in a controlled fashion. In the present invention, atomization is achieved by imposition of relatively high pressure that forces the liquid through a relatively small nozzle which breaks the fluid into droplets.

It may be appreciated that the adapter allows for the modification of syringe to provide an atomizer. The geometry and configuration of the adapter, including the size of the adapter guide, pin, pin guide and spring may be adjusted depending on the configuration and size of the syringe. In particular, the pin size can be varied to accommodate different needle sizes to produce the same or similar spray patterns. Further, the atomizer may be removable and transferred onto one or more syringes. Finally, the device may provide a relatively high precision low dose spray.

EXAMPLE

An organic test fluid was sprayed from a 50 microliter and a 100 microliter HAMILTON gas tight syringe with a cemented style 22 gauge needle including an atomizing device described herein mounted thereon.

The fluid was captured within a small vial. The captured volume was determined by the net weight of the vial, which converted to volume via a fluid density, the standard deviation, average percentage of the target and relative standard deviation were determined. The net change in the weight of syringe was also converted to volume and the average percentage of target and relative standard deviation were determined. The test was performed five times at each target volume. The results are provided in Table 2 below.

TABLE 2

Test Results

| | | Captured in Vial | | | | Dosed from Syringe | |
|---|---|---|---|---|---|---|---|
| Target μL | Syringe Size μL | Captured Ave. μL | SD μL | Ave % Target % | RSD % | Ave % Target % | RSD % |
| 5.0 | 50 | 4.1 | 0.13 | 83% | 3.5% | 100% | 5.1% |
| 13 | 50 | 12 | 0.35 | 93% | 3.4% | 100% | 1.7% |
| 25 | 50 | 24 | 0.34 | 95% | 1.6% | 100% | 0.9% |
| 85 | 100 | 81 | 1.0 | 96% | 1.5% | 98% | 0.9% |

Figure 9:
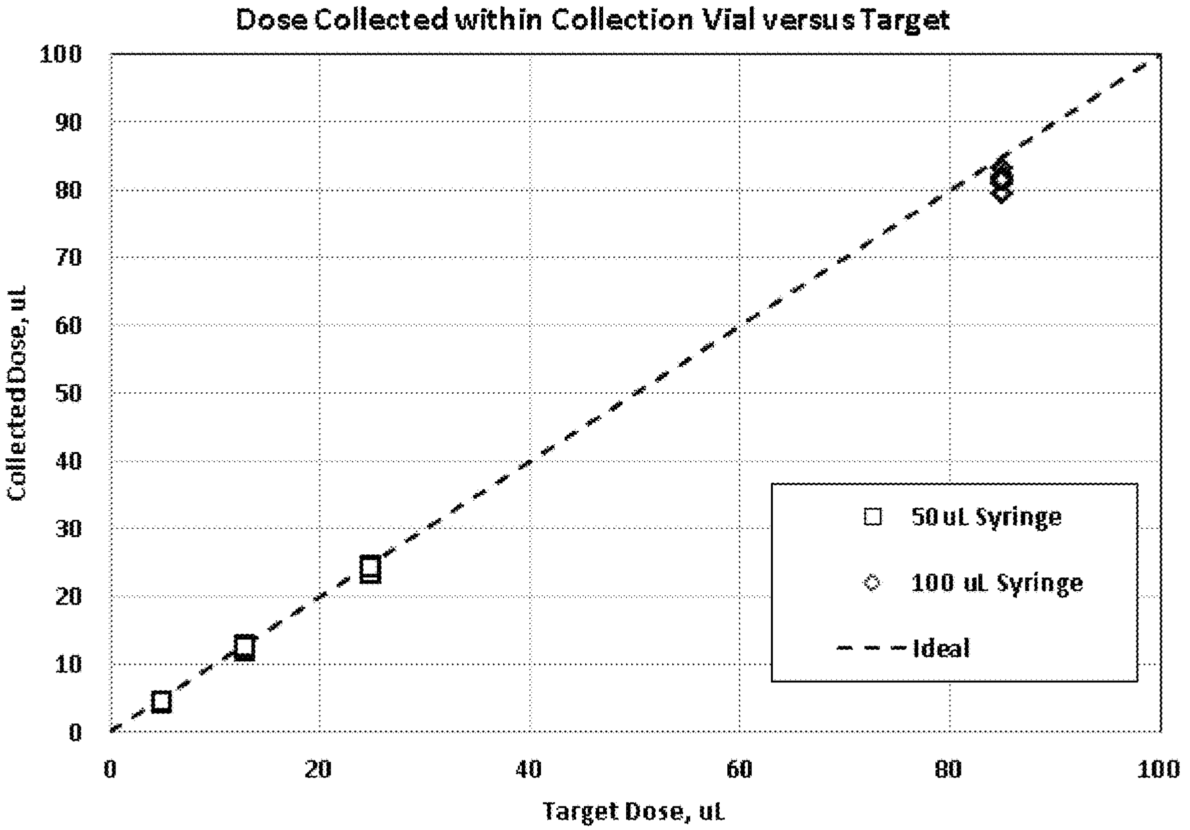
FIG. 9 is a graph of target dose versus collected dose.

It is noted that SD is the standard deviation, Ave % Target is the average percentage of the target captured and RSD is the relative standard deviation. FIG. 9 illustrates the captured dose versus the target does. It is believed the lost mass is due to capture inefficiency and evaporation of residue from the nozzle surface.

The foregoing description has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

The invention claimed is:

1. An atomizing delivery device, comprising:

a syringe including a barrel and a cannula extending from said barrel, wherein said cannula includes a terminal opening;

an adapter comprising:

an adapter guide including a side wall, an interior surface of said side wall defining a through-bore and a shoulder in said through-bore;

wherein said cannula is located in said through-bore;

a pin guide including a seat and a sleeve extending from said seat and said pin guide is located in said through-bore and surrounds a portion of said cannula;

a spring positioned around said pin guide sleeve and between said pin guide seat and said shoulder, wherein said spring and said sleeve provide a passageway therebetween; and a pin extends through said passageway from said pin guide and said pin is seated on said terminal opening of said cannula.

2. The device of claim 1, wherein a portion of said barrel is received in a portion of said adapter guide, and said adapter guide and said syringe exhibit an interference fit.

3. The device of claim 1, wherein said cannula is a cannula of a needle.

4. The device of claim 3, wherein said needle includes a needle hub and said needle is affixed to said syringe barrel by said needle hub.

5. The device of claim 1, wherein said terminal opening is blunt or beveled.

6. The device of claim 1, wherein said pin includes a stem, which extends through said passageway and an arm extending from said stem, wherein said arm exhibits a conical tip and is received in said terminal opening.

7. The device of claim 1, wherein said syringe holds 5 μL to 100 μL of a liquid formulation.

8. An adapter for delivering an atomized spray from a syringe, comprising:

an adapter guide including a side wall, an interior surface of said side wall defining a through-bore and a shoulder in said through-bore;

a pin guide located within said through-bore, said pin guide including a seat and a sleeve extending from said seat;

a spring positioned around said pin guide sleeve and between said pin guide seat and said shoulder, wherein said spring and said sleeve provide a passageway therebetween;

a pin extending from said pin guide seat and through said passageway.

9. The adapter of claim 8, wherein said adapter guide includes a proximal opening and a distal opening, and a portion of said pin extends out from said distal opening.

10. The adapter of claim 8, wherein said through-bore includes a first portion to receive said syringe.

11. The adapter of claim 8, wherein said pin includes a stem and an arm extending from an end of said stem opposing said pin guide seat.

12. The adapter of claim 11, wherein said arm includes a conical tip.

13. The adapter of claim 11, wherein said pin guide seat includes a channel for receiving an end of said spring and a bore for receiving a second end of said pin stem opposing said arm.

14. A method of dispensing an atomized spray from a syringe, comprising:

affixing an adapter to a syringe, wherein said syringe includes: a barrel including a liquid formulation, and a cannula extending from the barrel, and said adapter comprises: an adapter guide including a side wall, an interior surface of said side wall defining a through-bore and a shoulder in said through-bore, wherein said cannula is inserted into said through-bore and said cannula includes a terminal opening, a pin guide including a seat and a sleeve extending from said seat located within said through-bore and a portion of said cannula is passed through said pin guide, a spring positioned around said pin guide sleeve and between said pin guide seat and said shoulder, wherein said spring and said sleeve provide a passageway therebetween, and a pin extending through said passageway from said pin guide and said pin is seated on said terminal opening; and dispensing said liquid formulation from said syringe as an atomized spray.

15. The method of claim 14, wherein said adapter is affixed to said syringe by press fitting said adapter onto said syringe.

16. The method of claim 14, wherein said cannula is a needle.

17. The method of claim 14, wherein said liquid formulation is dispensed by applying a force to said liquid formulation in said barrel and disengaging said pin from said terminal opening with said liquid formulation.

18. The method of claim 14, wherein said liquid formulation is dispensed by forcing a plunger in said barrel towards said cannula.

19. The method of claim 14, wherein said liquid formulation comprises a pharmaceutical composition.

* * * * *